(12) United States Patent
Zweber et al.

(10) Patent No.: US 9,061,132 B1
(45) Date of Patent: Jun. 23, 2015

(54) POSITIONING OF A MEDICAL DEVICE CONDUCTOR IN AN MRI ENVIRONMENT TO REDUCE RF INDUCED CURRENT

(75) Inventors: Jeffrey Zweber, St. Louis Park, MN (US); Robert Shawn Johnson, North Tonawanda, NY (US)

(73) Assignee: Greatbatch Ltd., Clarence, NY (US)

( * ) Notice: Subject to any disclaimer, the term of this patent is extended or adjusted under 35 U.S.C. 154(b) by 359 days.

(21) Appl. No.: 13/400,701

(22) Filed: Feb. 21, 2012

Related U.S. Application Data

(60) Provisional application No. 61/444,182, filed on Feb. 18, 2011.

(51) Int. Cl.
*A61N 1/00* (2006.01)

(52) U.S. Cl.
CPC ........................................ *A61N 1/00* (2013.01)

(58) Field of Classification Search
USPC .................. 607/2, 9, 115, 116, 120, 121, 122
See application file for complete search history.

(56) References Cited

U.S. PATENT DOCUMENTS

| | | |
|---|---|---|
| 5,143,090 A | 9/1992 | Dutcher et al. |
| 5,217,010 A | 6/1993 | Tsitlik et al. |
| 5,255,693 A | 10/1993 | Dutcher et al. |
| 6,585,763 B1 * | 7/2003 | Keilman et al. ............... 623/1.42 |
| 6,613,474 B2 | 9/2003 | Frustaci et al. |
| 7,363,090 B2 | 4/2008 | Halperin et al. |
| 7,640,064 B2 | 12/2009 | Swoyer |
| 7,899,551 B2 | 3/2011 | Westlund et al. |
| 2007/0112398 A1 | 5/2007 | Stevenson et al. |
| 2008/0049376 A1 | 2/2008 | Stevenson et al. |
| 2008/0071313 A1 | 3/2008 | Stevenson et al. |
| 2008/0116997 A1 | 5/2008 | Dabney et al. |
| 2008/0132987 A1 | 6/2008 | Westlund et al. |
| 2011/0144734 A1 | 6/2011 | Westlund et al. |
| 2011/0230943 A1 | 9/2011 | Johnson et al. |

* cited by examiner

*Primary Examiner* — Catherine Voorhees
*Assistant Examiner* — Nadia A Mahmood
(74) *Attorney, Agent, or Firm* — Steven W. Winn; Michael F. Scalise

(57) ABSTRACT

The present invention provides embodiments in which induced RF current heating along the length of a medical lead is reduced. Reduction of induced RF current heating in the medical lead is achieved by positioning a conductor about the exterior of an implantable medical device when the device is placed within an MRI environment. In one embodiment, an RF conductor is incorporated within a header assembly for connecting an implantable medical device to at least one conductor lead. The body of the RF conductor is positioned circumferentially around the implantable medical device. In another embodiment, the medical lead is positioned circumferentially around the exterior of the housing of the medical device. A series of clips or a sleeve holds the medical lead or RF conductor in place around the device.

32 Claims, 9 Drawing Sheets

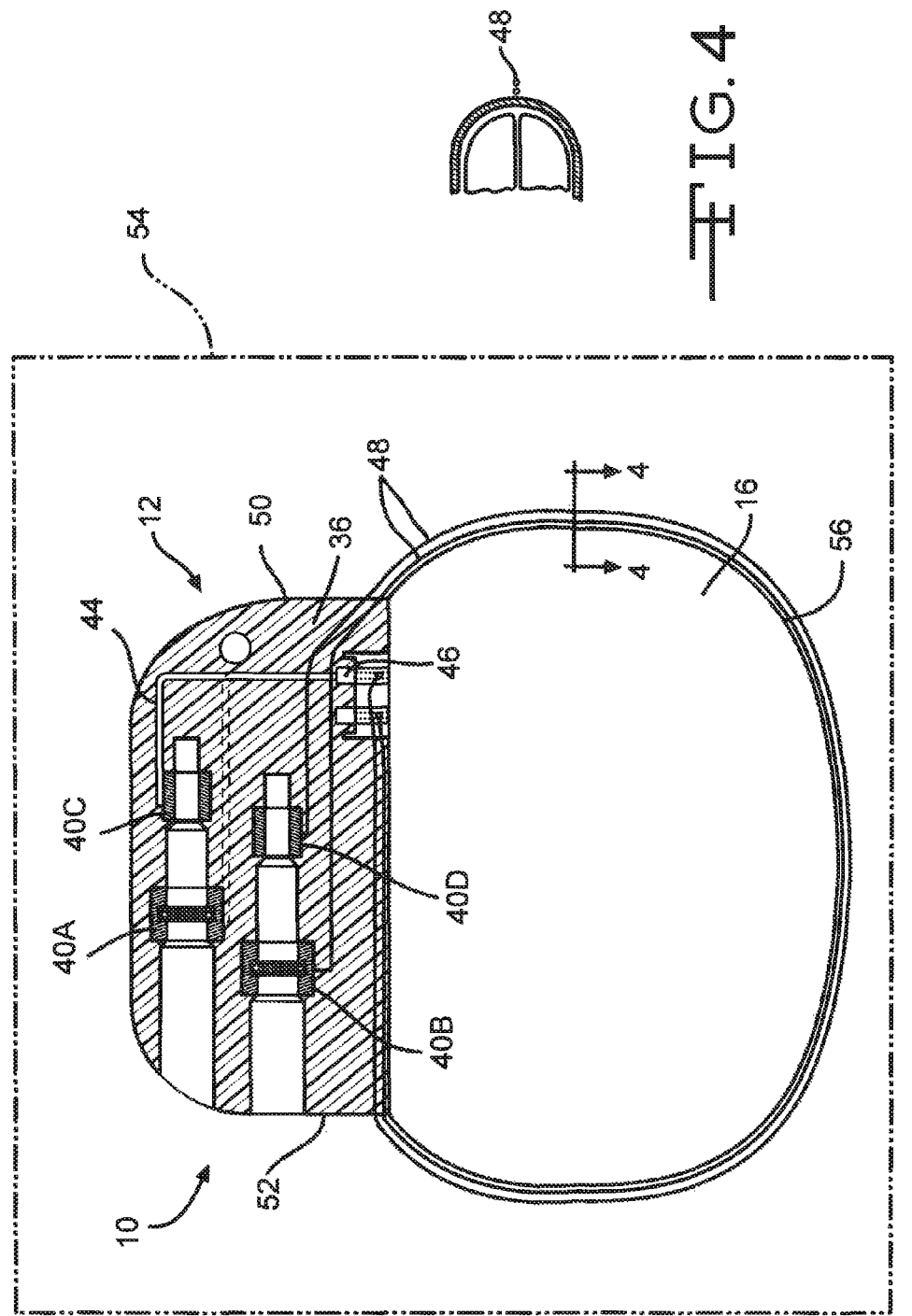

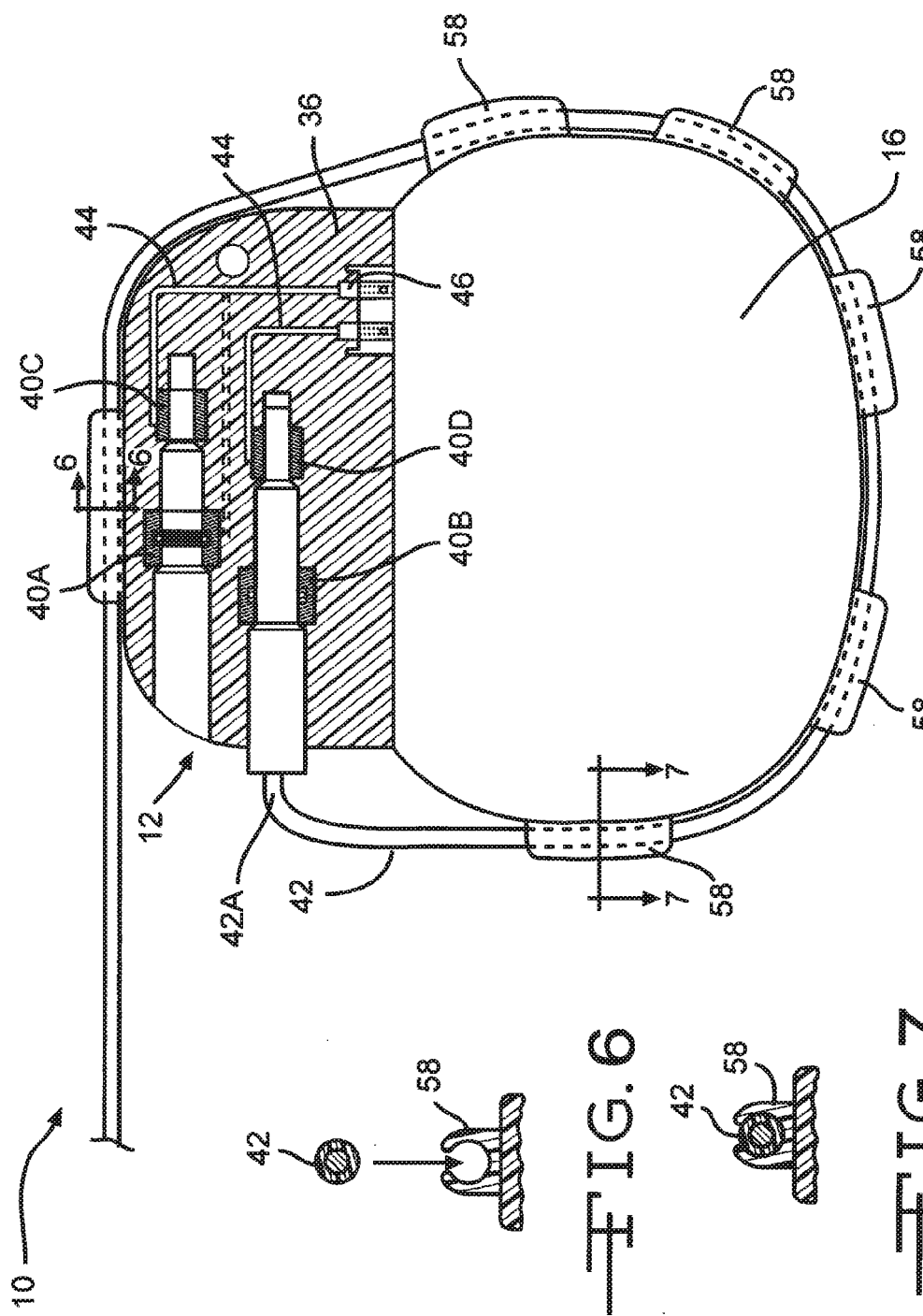

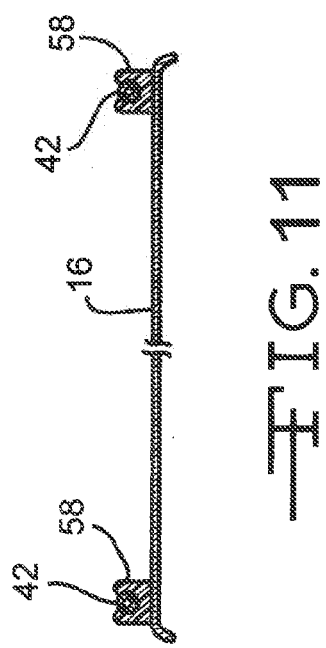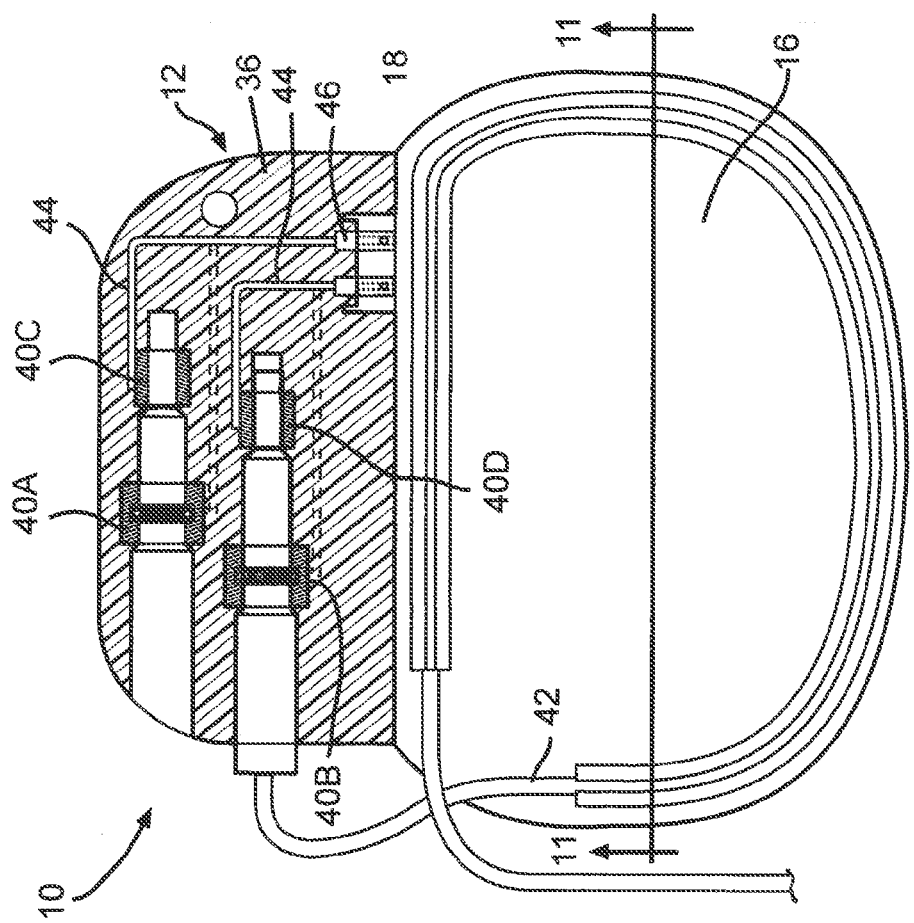

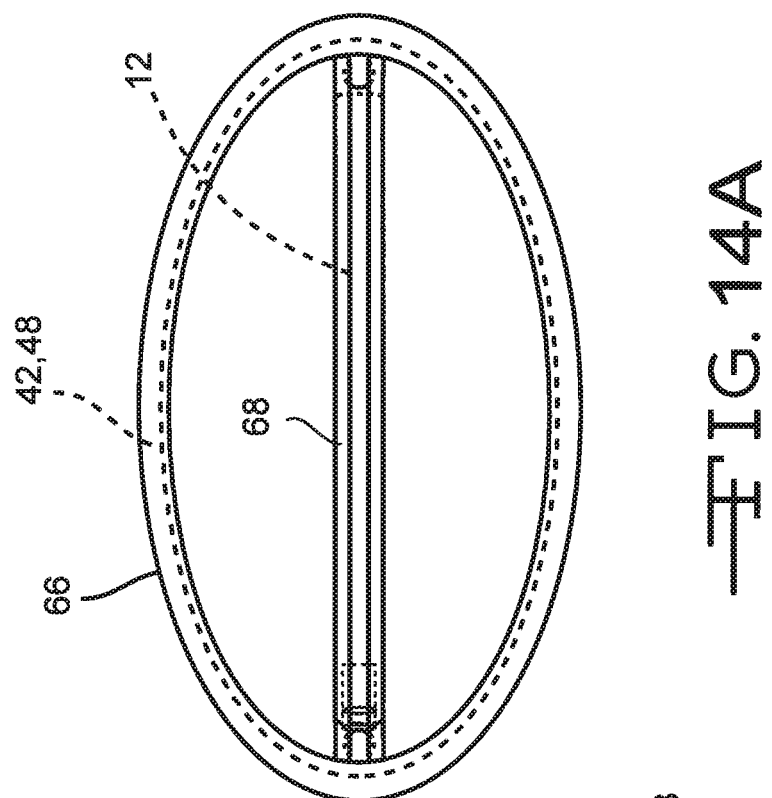
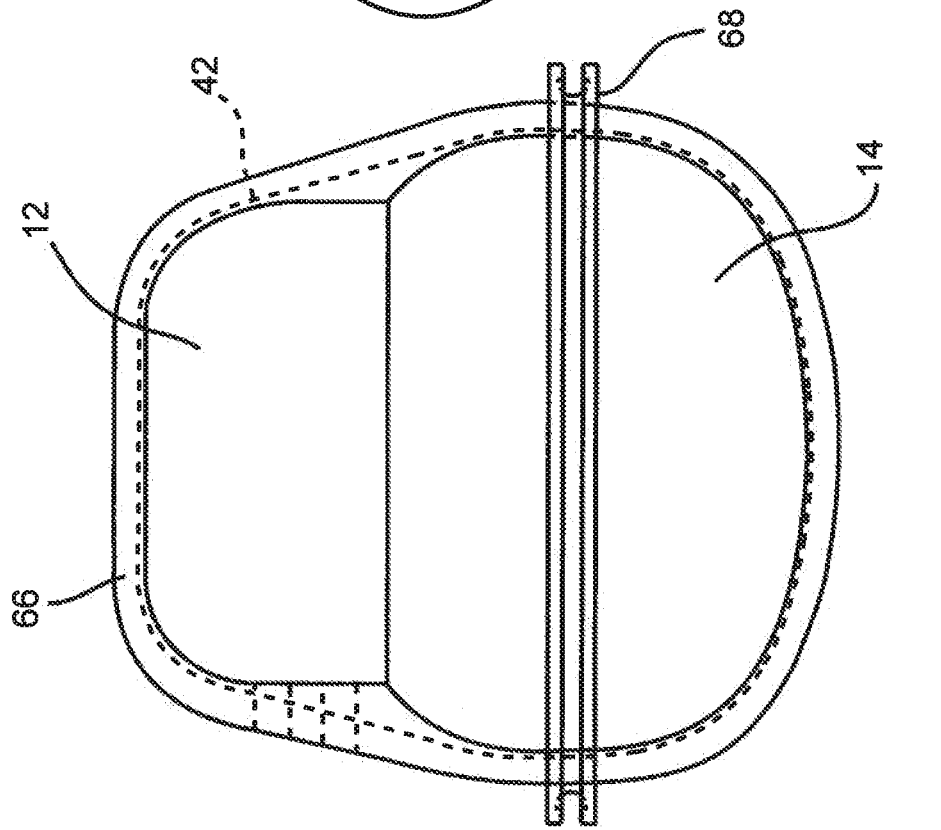

POSITIONING OF A MEDICAL DEVICE CONDUCTOR IN AN MRI ENVIRONMENT TO REDUCE RF INDUCED CURRENT

CROSS-REFERENCE TO RELATED APPLICATIONS

This application claims priority from U.S. Provisional Patent Application Ser. No. 61/444,182, filed Feb. 18, 2011.

FIELD OF THE INVENTION

This invention relates generally to a means of positioning a conductor about an implantable medical device such that RF lead tip heating is reduced when the medical device is placed within an MRI environment.

BACKGROUND OF THE INVENTION

The radio frequency (RF) pulsed field of MRI can couple to an implanted lead in such a way that electromagnetic forces (EMFs) are induced in the lead. The amount of energy that is induced is related to a number of complex factors, but in general, is dependent upon the local electric field that is tangent to the lead and the integral of the subsequent electric field strength along the lead. In certain situations, these EMFs can cause currents to flow into distal electrodes and through the electrode interface to body tissue. It has been documented that when this current becomes excessive, overheating of the lead and the adjacent body tissue can occur. There have been cases of damage to both myocardial tissue and neurological tissue. In some cases, damage severe enough to result in loss of therapy, ablation, brain damage, limb amputations, and the like have occurred.

Magnetic resonance imaging (MRI) is one of medicine's most valuable diagnostic tools. MRI is, of course, extensively used for imaging, but is also used for interventional medicine (surgery). In addition, MRI is used in real time to guide ablation catheters, neurostimulator tips, deep brain probes, and the like. An absolute contra-indication for pacemaker or neurostimulator patients means that these patients are excluded from MRI. This is particularly true of scans of the thorax and abdominal areas.

Because of MRI's incredible value as a diagnostic tool for imaging organs and other body tissues, many physicians simply take the risk and go ahead and perform MRI on a patient who may have any one of a number of active implantable medical (AIMD) devices. The literature indicates a number of precautions that physicians should take in such cases, including limiting the power of the MRI RF pulsed field (Specific Absorption Rate or SAR level), programming the pacemaker to fixed or asynchronous pacing mode, and then careful reprogramming and evaluation of the pacemaker and patient after the procedure is complete. There have been reports of latent problems with cardiac pacemakers or other AMDs after an MRI procedure, sometimes occurring many days later. Moreover, there are a number of papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI scanner. The first type is the main static magnetic field designated $B_0$, which is used to align protons in body tissue. The field strength varies from 0.5 to 3.0 Tesla in most of the commonly available MRI units in clinical use. Some of the newer research MRI system fields can go as high as 11.7 Tesla or more.

The second type of field produced by magnetic resonance imaging is the pulsed RF field, which is generated by the body coil or head coil of the MRI instrument. The body coil is generally used to change the energy state of the protons and elicit MRI signals from tissue. The RF field is typically homogeneous in the central region and has two main components: (1) the electric field is circularly polarized in the actual plane; and (2) the $B_1$ field, sometimes generally referred to as the net magnetic field in matter, is related to the electric field by Maxwell's equations and is relatively uniform. In general, the RF field is switched on and off during measurements and usually has a frequency of between about 21 MHz to about 500 MHz depending upon the static magnetic field of the MRI scanner. The frequency of the RF pulse for hydrogen scans varies by the Lamour equation with the field strength of the main static field where: RF PULSED FREQUENCY in MHz=42.56 (STATIC FIELD STRENGTH IN TESLA). MRI scanners employing NMR-like functionality are also capable of detecting ions with different gyromagnetic constants.

The third type of electromagnetic field is the time-varying magnetic gradient fields designated $G_X$, $G_Y$, $G_Z$, which are used for spatial localization. These change their strength along different orientations and operating frequencies on the order of 2-5 kHz. The vectors of the magnetic field gradients in the X, Y and Z directions are produced by three sets of orthogonally positioned coils and are switched on only during the operation of the MRI scanner.

The power deposited by RF pulses during MRI is complex and is dependent upon many factors including, power (Specific Absorption Rate (SAR) Level), duration time of the RF pulse, transmission frequency, the number of RF pulses applied per unit time, and the type of configuration of the RF transmitter coil used. The amount of resultant heating also depends upon the volume of tissue imaged, the electrical resistivity of tissue and the configuration of the anatomical region imaged. There are also a number of other variables that depend on the placement in the human body of the AMD and the length and trajectory of its associated lead(s). For example, even whether a pacemaker is positioned in the left or right pectoral will affect the amount of EMF that is induced into a pacemaker lead system. In addition, the routing of the lead and the lead length are also very critical as to the amount of induced current and heating that would occur.

Variations in the device lead length and implant trajectory can significantly affect how much heat is generated. A paper entitled, "HEATING AROUND INTRAVASCULAR GUIDEWIRES BY RESONATING RF WAVES" by Konings, et al., Journal of Magnetic Resonance Imaging, Issue 12:79-85 (2000), does an excellent job of explaining how the RF fields from MRI scanners can couple into implanted cardiac leads. The paper includes both a theoretical approach and actual temperature measurements. In a worst-case, they measured temperature rises of up to 74° C. after 30 seconds of scanning exposure. The contents of this paper are incorporated herein by reference.

Distal electrodes can be unipolar, bipolar, multipolar and the like. It is very important that excessive RF current not flow at the interface between the lead distal tip electrode or electrodes and body tissue. In a typical cardiac pacemaker, for example, the distal tip electrode can be passive or of a screw-in helix type as will be more fully described. In any event, it is very important that excessive RF current not flow at this junction between the distal tip electrode and, for example, into surrounding cardiac or nerve tissue. Excessive current at the distal electrode to the tissue interface can cause excessive heating to the point where tissue ablation or even perforation can occur. This can be life-threatening for cardiac patients. For neurostimulator patients, such as deep brain stimulator patients, thermal injury can cause permanent disability, debilitating comas or even be life threatening. Similar issues exist for spinal cord stimulator patients, cochlear implant patients, and the like.

A very important and possibly life-saving solution is to be able to control overheating of implanted leads during an MRI procedure. A novel and very effective approach to this is to first install parallel resonant inductor and capacitor bandstop filters (BSF) at or near the distal electrode of implanted leads. For cardiac pacemakers, these are typically known as the tip and ring electrodes. One such bandstop filter (BSF) solution is disclosed in U.S. Pat. No. 7,363,090 to Halperin et al. as well as U.S. Pat. Nos. 7,945,322, 7,853,324 to Stevenson et al., U.S. Pat. No. 7,899,551 to Westlund et al., U.S. Pat. No. 7,853,325 to Dabney et al. and patent application publication number, 2008/0049376 to Stevenson et al., all of which are assigned to the assignee of the present invention and are incorporated by reference herein.

Other types of component networks may also be used in implantable leads to raise their impedance at MRI frequencies and, therefore, reduce RF induced heating. For example, a series inductors may be used as a single element low pass filter. When positioned within an active MRI environment, the inductance of these component networks tends to increase at high frequencies, such as the RF pulsed frequencies of a typical MRI scanner, which inhibits RF lead heating. Component networks such as these are disclosed in U.S. Pat. No. 5,217,010 to Tsitlik et al. the contents of which are incorporated herein by reference.

U.S. Pat. No. 7,363,090 shows resonant L-C bandstop filters placed at the distal tip and/or at various locations along the medical device leads or circuits. These L-C bandstop filters inhibit or prevent current from circulating at selected frequencies of the medical therapeutic device. For example, for an MRI system operating at 1.5 Tesla, the pulsed RF frequency is 63.84 MHz, as described by the Lamour Equation for hydrogen. The L-C bandstop filter is generally designed to resonate at or near 63.84 MHz, thus creating a higher impedance that establishes an ideal open circuit in the lead system at that selected frequency. For example, the L-C bandstop filter when placed at the distal tip electrode of a pacemaker lead will significantly reduce RF currents from flowing through the distal tip electrode and into body tissue.

However, a drawback associated with these filtering solutions is that they generally take up space within the lead, particularly at the distal end of the lead. In many cases, it is difficult to incorporate these filtering solutions within a small diameter lead or a lead comprising a multitude of electrodes such as a neurostimulator. For example, a neurostimulator lead may comprise 6, 12, 16 or more electrodes, each of which may require a filter to reduce RF heating. In addition, implantable medical devices with intricately small leads, such as deep brain stimulators, make incorporating a component filtering solution prohibitively difficult.

Accordingly, there is a need for reducing RF heating in leads of implantable medical devices such as neurostimulators comprising a multitude of electrodes. Furthermore, there is a need for reducing RF heating in leads of implantable medical devices in which the leads are prohibitively small for use of component based RF filtering solutions. The present invention fulfills these needs and provides other related advantages.

SUMMARY OF THE INVENTION

The present invention provides embodiments in which RF current induced heating along the length of a medical lead is reduced. Reduction of RF current induced heating in the medical lead is achieved by positioning a conductor about the exterior of the implantable medical device when the device is placed within an MRI environment. The conductor may be positioned about the exterior of the medical device either, before, during or after the time of implant of the device.

In one embodiment of the present invention, a header assembly is provided in which a RF conductor, specifically a RF conductive wire or RF conductive filar, is positioned circumferentially around the exterior of the implantable medical device. In this embodiment, the RF conductive wire or wires are positioned around the exterior in close proximity to the exterior surface of the housing of the medical device. More specifically, at least one conductive wire or filar is positioned such that an electrical connection is formed between the proximal end of a medical lead and a connector of the assembly. The header assembly connector establishes an electrical connection between the circuitry of the medical device and the RF conductor. Specifically, the RF conductor wire is positioned such that its proximal and distal ends reside within the header assembly and the body of the conductor extends around the exterior of the medical device. Therefore, in this embodiment, an electrical connection between the medical lead and the electrical circuitry is established by the RF conductor. The RF conductor may be insulated, or otherwise isolated from the exterior surface of the device to prevent unwanted coupling or signal loss.

In another embodiment of the present invention, the proximal end of a conductor lead, i.e. a medical device lead, is first inserted into the header assembly, the extending portion of the lead is positioned in a controlled manner about the perimeter of the device. More specifically, once the proximal end of the conductor lead is electrically connected within the header assembly, a portion of the conductor lead is positioned such that it is in close proximity with the exterior surface of the housing of the medical device. Alternatively, the conductor lead could be positioned such that it lies along an exterior sidewall surface of the housing of the medical device. In either case, the conductor lead is positioned such that it is exterior to the medical device and extends along the perimeter of the device. A clip or sleeve residing along the exterior surface of the medical device may be used to secure the desired portion of the conductor lead to the exterior surface of the medical device.

Experimental data has been generated that indicates that placement of the conductor lead or medical lead directly affects the degree to which the lead electrodes heat when situated within an active MRI environment. Specifically, the experimental data shows that when the medical lead is positioned about the exterior of the medical device, in a particular fashion, the measured increase in heat along the lead electrodes is reduced. It is therefore believed that the position of a conductor in a controlled manner about the medical device reduces the amount of induced RF current within the medical lead as shown by the measured decrease in lead heating when residing with an MRI environment.

BRIEF DESCRIPTION OF THE DRAWINGS

FIG. 3 shows a conductive wire positioned about the perimeter of an implantable medical device according to an embodiment of the present invention.

FIG. 4 shows a cross-sectional view along line 4-4 illustrating the two conductive wires positioned along the exterior of the housing of the device.

FIG. 5 illustrates an implantable medical device in which a medical lead is positioned about the exterior of the device.

FIG. 6 shows a cross-sectional view of an embodiment of a medical lead being positioned within a lead clip.

FIG. 7 illustrates a cross-sectional view taken along line 7-7 of the embodiment shown in FIG. 5.

FIG. 10 shows an alternate embodiment of the present invention in which a medical lead is positioned about the exterior side of the housing of a medical device.

FIG. 11 shows a cross-sectional view of the embodiment shown in FIG. 10 taken along line 11-11.

FIG. 14 shows a side view of an alternate embodiment in which a band is positioned around the medical device.

FIG. 14A illustrates a top view of the alternate embodiment shown in FIG. 14.

DETAILED DESCRIPTION OF THE INVENTION

Figure 1:
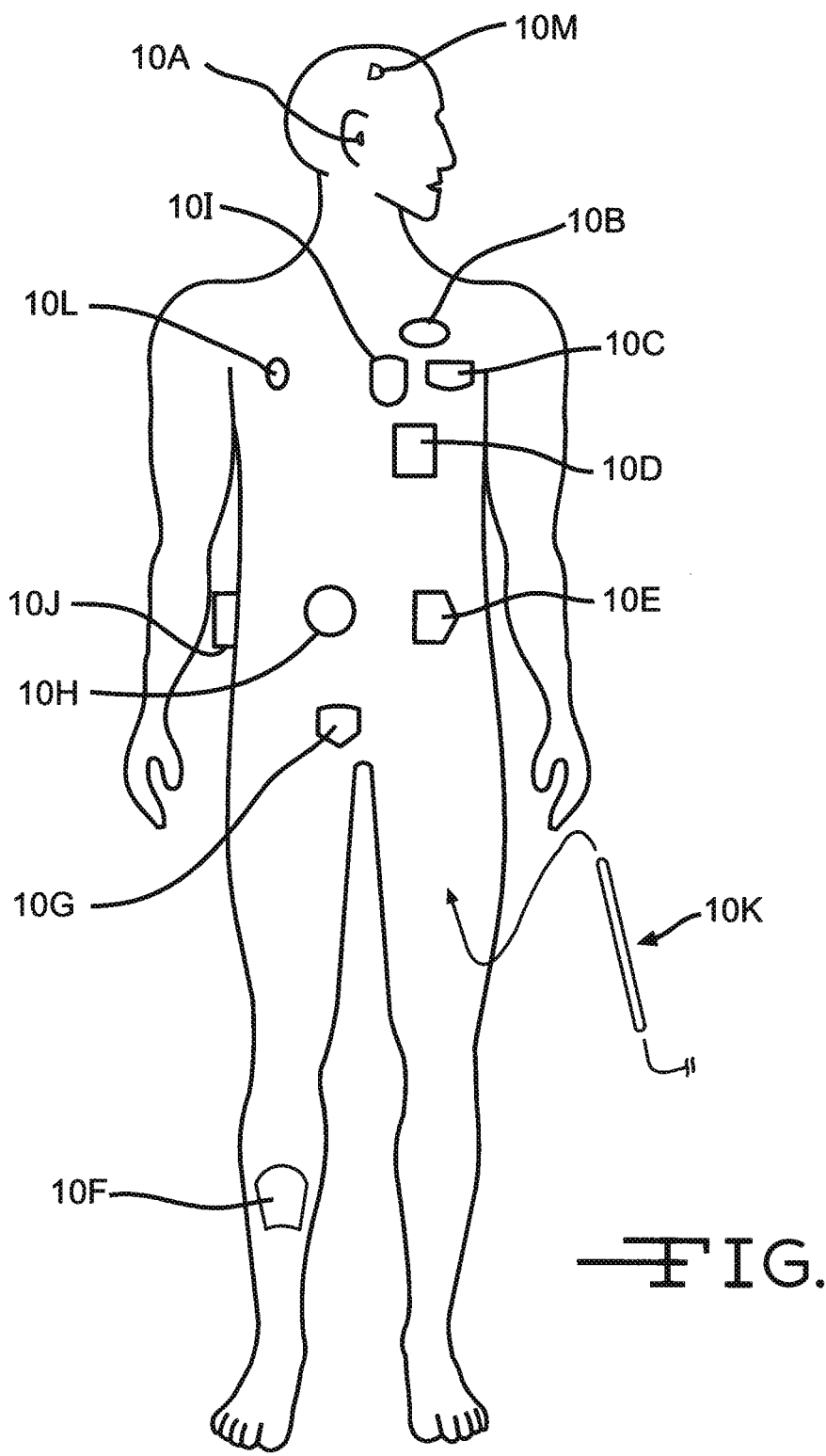
FIG. 1 illustrates various non-limiting examples of active implantable medical devices that could utilize the present invention.

As shown in the drawings for purposes of illustration, the present invention pertains to the placement of a conductor about an active implantable medical device (AIMD) such that induced RF current heating within the medical lead, particularly of the electrodes of the medical lead, of the connected medical device is reduced. More specifically, the present invention concerns the controlled placement of the conductor about the exterior of an implantable medical device, for example as a cardiac pacemaker, a cardioverter defibrillator, or a neurostimulator, such that when the device is placed within an MRI environment, RF current induced heating within its connected lead is reduced.

The term "conductor" is herein defined as an electrically conductive pathway. The conductor may comprise a single electrically conductive wire, filar, filled via, conductive trace, such as a conductive line deposited on a surface, or may comprise a plurality of electrically conductive wires, filars or filled vias. The term "filar" is herein defined as a strand of electrically conductive material. The term "wire" is herein defined as a metallic strand or rod that conducts electricity. A wire may be comprised of a monolithic structure or of a composite structure, such as a combination of metals. Examples of composite wire structures include, but are not limited to, a dual drawn wire, drawn filled tube, a clad coating and the like in a woven, braided, wound, twisted or other form that is commonly known in the art. The term "conductor lead" is herein defined as a composite of wire or filer strands that directs the flow of electrical energy and/or electrical signals. The terms "conductor lead" and "medical lead" are herein defined to be the same and may be used interchangeably.

As shown in FIG. 1, the present invention can be utilized with a plurality of external and implantable medical devices 10. Non-limiting examples include hearing devices 10A which may include cochlear implants, piezoelectric sound bridge transducers, and the like. Numerical designation 10B represents a variety of neurostimulators, neuromodulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of a seizure and also providing electrical stimulation to brain tissue to prevent the seizure from actually occurring. As noted above, it would be a significant improvement in surgical technique if the lead wires associated with a deep brain stimulator could be placed using real time MRI imaging.

Numerical designation 10C shows a cardiac pacemaker which is well-known in the art. Numerical designation 10D includes the family of left ventricular assist devices (LVAD's), and artificial hearts, including the recently introduced artificial heart known as the Abiocor. Numerical designation 10E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. Numerical designation 10F includes a variety of bone growth stimulators for rapid healing of fractures. Numerical designation 10G includes urinary incontinence devices. Numerical designation 10H includes the family of pain relief spinal cord stimulators and anti-tremor stimulators. Numerical designation 10H also includes an entire family of other types of neurostimulators used to block pain. Numerical designation 10L includes a family of implantable cardioverter defibrillators (ICD) devices and also includes the family of congestive heart failure devices (CHF). This is also known in the art as cardio resynchronization therapy devices, otherwise known as CRT devices. Numerical designation 10J illustrates an externally worn pack. This pack could be an external insulin pump, an external drug pump, an external neurostimulator or even a ventricular assist device. Numerical designation 10K illustrates the insertion of an external probe or catheter. These probes can be inserted into the femoral artery, for example, or in any other number of locations in the human body. Numerical designation 10L illustrates one of various types of EKG/ECG external skin electrodes which can be placed at various locations. Numerical designation 10M are external EEG electrodes placed on the head.

Figure 2:
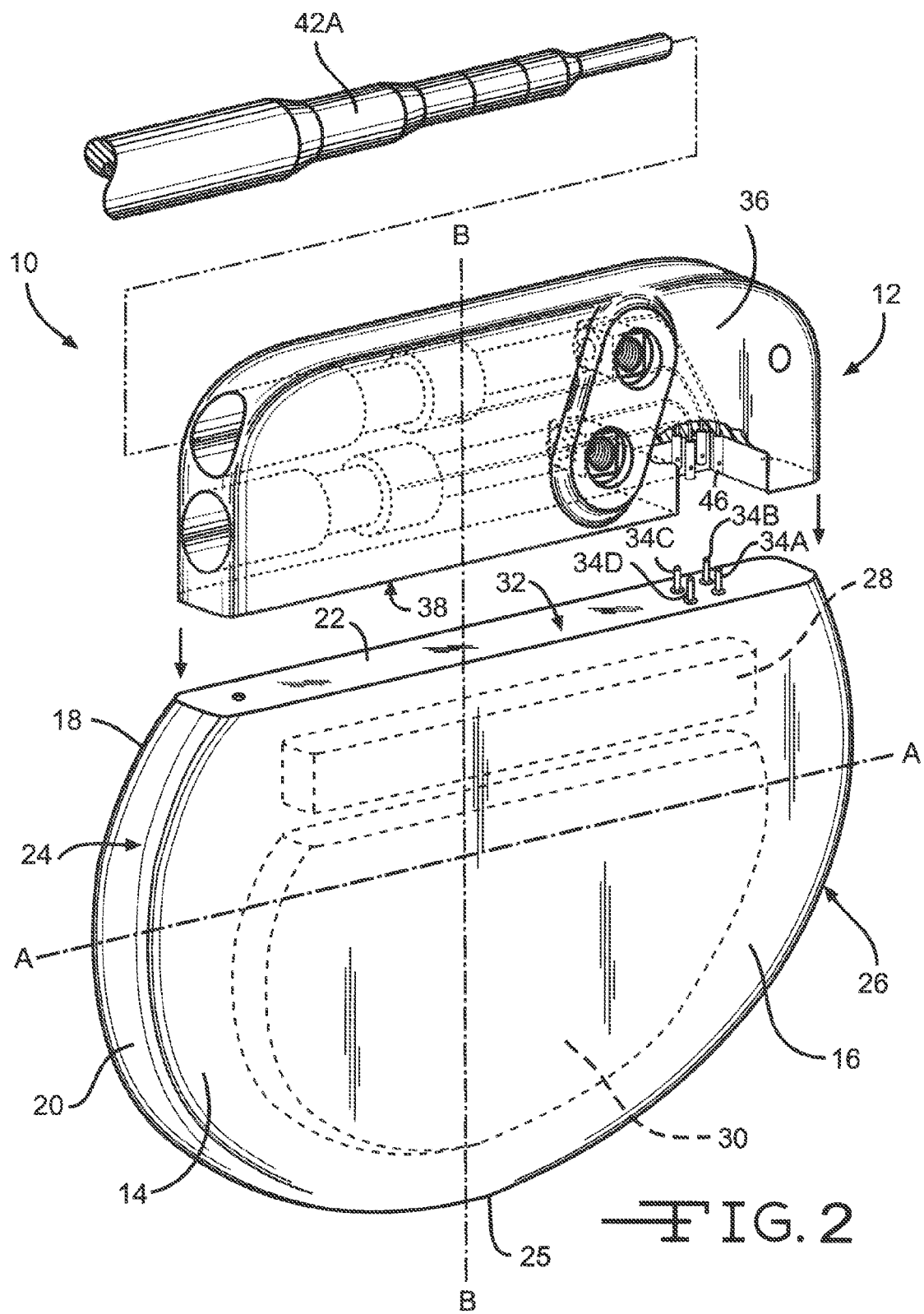
FIG. 2 illustrates an exploded view of an embodiment of a header assembly mounted on an implantable medical device according to the present invention.

FIG. 2 is an exploded view of a header assembly 12 mounted on an implantable medical device 10 according to an embodiment of the present invention. The exemplar implantable medical device 10 comprises a housing 14. The device housing 14 may be composed of a conductive material, such as of titanium or stainless steel. Alternatively, the housing 14 may be composed of an insulating material such as a ceramic material. The medical device housing 14 is preferably comprised of mating two housing halves, similar to that of a clam shell, in an overlapping or butt welded construction, as shown in U.S. Pat. No. 6,613,474 to Frustaci et al. This patent is assigned to the assignee of the present invention and incorporated herein by reference. The housing 14 can also be of a deep drawn, prismatic and cylindrical design, as is well known to those skilled in the art.

Longitudinal axis A-A and perpendicular axis B-B are shown to establish orientation about the device 10. For purposes of orientation, the term "equitorial" refers to the general direction along longitudinal axis A-A. The term "longitudinal" refers to the general direction along perpendicular axis B-B.

The housing 14 is shown in an exemplary form comprising first and second planar major face walls 16 and 18 joined together by a sidewall 20 and a housing header wall 22. The sidewall 20 curves from one end of the header wall 22 to the other end having respective left and right sidewall surfaces 24, 26. The housing sidewall 20 is generally arcuate from face wall 16 to face wall 18. The preferred mating clam shells of the housing 14 are hermetically sealed together, such as by laser or resistance welding, to provide an enclosure for the medical device including its control circuitry 28 and a power supply 30, such as an electrochemical cell (the control circuitry and power supply are shown in dashed lines in FIG. 2). The power supply 30 is connected to the control circuitry 28 by electrical leads (not shown). There may also be a capacitor for a medical device such as a defibrillator. The implantable medical device 10 is exemplary of any one of a number of known assist devices such as cardiac defibrillators, cardiac pacemakers, drug pumps, neurostimulators, hearing assist devices, and the like as previously discussed.

Header wall 22 of the housing 14 has a planar upper surface 32 providing at least one opening through which a feedthrough conductor passes. In the embodiment depicted in FIG. 2, the upper surface 32 of housing 14 includes four openings through which respective feedthrough conductors 34A, 34B, 34C, and 34D pass. The feedthrough conductors extend from a proximal end positioned within the housing 14 connected to the control circuitry 28 to respective distal ends spaced above the housing upper surface 32. The feedthrough conductors 34A, 34B, 34C, and 34D are electrically insulated from the housing 14 by respective ceramic-to-metal seals or glass-to-metal seals (not shown), as are well known by those skilled in the art.

As shown in FIGS. 2-3, 5 and 10, the header assembly 12 is comprised of an insulative body 36 that is mountable along its bottom surface 38 to the upper surface 32 of the housing 14 of the medical device 10. The header assembly 12 comprises a conductor subassembly comprising a terminal 40 supported by the insulative body 36. As illustrated in FIG. 3, there are four terminals, distal terminals 40A and 40B and proximal terminals 40C and 40D. In a preferred embodiment, each conductor lead, i.e. medical lead 42, makes electrical contact with a proximal and distal terminal 40A, 40C when inserted in the header assembly 12. As shown, a conductor lead proximal end portion 42A is inserted within the header assembly 12 to establish electrical contact with the device 10. Therefore, the number of terminals is dependent upon the number of conductor leads 42 that are inserted within the header assembly 12. For example, a header assembly designed for a single conductor lead may comprise two terminals 40A, 40C whereas a header assembly for six conductor leads 42 may comprise a total of 12 terminals 40; a proximal and distal terminal for each of the conductor leads 42.

The conductor assembly may further comprise an intermediate conductor 44 comprising a distal end electrically connected to the terminal and a proximal end in electrical contact with a connector 46. Each connector 46 comprises an outer surface and a distal connector portion spaced from a proximal connector portion. In a preferred embodiment, the distal portion of the connector 46 is supported by the insulative body 36 of the header assembly 12 and the proximal connector portion is connectable to the at least one feedthrough conductor 34 of the implantable medical device 10. The connector 46 and intermediate conductor 44 are preferably composed of an electrically conductive material such as titanium, MP35N, platinum, palladium or stainless steel.

In a preferred embodiment, the header assembly 12 is composed of a polymeric material. Suitable polymeric materials include urethanes, such as e.g., TECOTHANE®, an aromatic polyether-based thermoplastic polyurethane sold by the Thermedics Polymeric Products Company of Wilmington, Mass.

FIG. 3 illustrates a preferred embodiment of the present invention wherein a RF conductor 48 such as a wire or filar, is positioned about the exterior surface of the AIMD 10. As illustrated, the distal end portion of the RF conductor 48 is attached to the terminal 40. More specifically, the distal end portion of the RF conductor 48 may either be connected to the distal terminal 40A, 40B or the proximal terminal 40C, 40D or both terminals 40A, 40B, 40C, 40D within the header assembly 12. The opposite proximal end portion of the RF conductor 48 is connected to one of the connectors 46, particularly the distal end portion of the connector 46 residing within the header assembly 12. The design feature of having both proximal and distal ends of the RF conductor 48 connected within the header assembly 12, provides additional mechanical strength to the attachment of the RF conductor 48 therefore reducing the possibility that the conductor 48 may become disconnected from its desired electrical connection.

The connection between the terminal 40 and the connector 46 by the RF conductor 48 provides electrical connection between the connected medical lead 42 and the internal circuitry of the medical device 10. In this case, the RF conductor 48 provides the electrical connection between the medical lead and the circuitry of the medical device, therefore the use of intermediate conductor 44 may not be necessary. However, it is contemplated that both or one of the intermediate conductor 44 and/or the RF conductor 48 may be used to establish an electrical connection between the lead conductor 42 and the medical device 10.

A single RF conductor 48 may be electrically connected to any of the plurality of terminals 40 within the header assembly 12. Alternatively, a plurality of RF conductors 48 may be electrically connected to a single terminal 40 or a multitude of terminals 40, respectively. At the opposite proximal end, the plurality of RF conductors 48 may be electrically connected to a plurality of respective connectors 46 or alternatively, the plurality of RF conductors 48 may be electrically connected to a single connector 46. In either case, the distal end portion of the RF conductor 48 is designed to be electrically connected to the terminal 40 and the proximal end portion of the RF conductor 48 connected to the connector 46.

Once the distal end portion of the RF conductor 48 is electrically connected to the terminal 40, the RF conductor 48 is preferably positioned such that it extends through the wall of the insulative body 36 of the header assembly 12. As illustrated in FIG. 3, the RF conductor 48 penetrates through a right sidewall 50 of the insulative body 36 of the header assembly 12. Alternatively, the header assembly 12 may be designed such that the RF conductor 48 penetrates through an opposite left sidewall 52. It is further contemplated that the RF conductor 48, once electrically joined to the proximal end portion 42A of the conductor lead 42, via terminal 40, may be positioned such that it penetrates through any sidewall of the insulative body 36 of the header assembly 12. For example, the RF conductor 48 may penetrate through the top, bottom, left, right, front or back sidewall of the header assembly 12.

As illustrated, the conductive RF conductor 48 is positioned about the exterior surface of the housing 14 of the AIMD. In a preferred embodiment, the RF conductor 48 is positioned such that it resides within an imaginary plane 54 that extends about parallel to longitudinal axis A-A, around the device 10 as shown in FIG. 3. More specifically, the RF conductor 48 is positioned circumferentially about the device 10 such that it extends from the exterior surface 26 of the right sidewall 50 of the housing 14, around the exterior surface of a bottom sidewall 56, to and around the exterior surface 24 of the left sidewall 52 of the housing 14 of the AIMD.

Alternatively, the RF conductor 48 may be positioned such that it lies about perpendicular to imaginary plane 54 along the exterior of the housing 14. In other words, the RF conductor 48 may be positioned about parallel to imaginary longitudinal axis A-A such that it generally extends equatorially along and around the face walls 16, 18 of the device 10. Likewise, the RF conductor 48 may be positioned about parallel to perpendicular axis B-B such that the conductor 48 extends from the bottom of the housing 14 to the top of the header assembly 12.

In either orientation, it is preferred that the RF conductor 48 is positioned such that it is in close proximity to the surface of the housing 14. More specifically, a portion of the RF conductor 48 may be positioned such that it is in physical contact with the exterior surface of the housing 14 of the AIMD. Furthermore, the RF conductor 48 may be positioned such that it resides from about 0.1 mm to about 5 mm away from the exterior surface of the AIMD.

In a preferred embodiment, the proximal end portion of the RF conductor 48 is attached to at least one of the conductor connectors 46 positioned within the header assembly 12. Alternatively, the proximal end portion of the RF conductor 48 may be connected to the feedthrough conductor 34A, 34B, 34C, 34C. Specifically, the proximal end portion of the RF conductor 48 may be connected to the distal end portion of the feedthrough conductor 34. The proximal end portion of the conductor 48 may be welded, crimped, swaged, soldered, or attached to the connector 46 or feedthrough conductor 34 with a conductive adhesive. In either method, the proximal end portion of the RF conductor 48 is electrically connected to at least one of the connectors 46 or feedthrough conductors 34A, 34B, 34C, 34D.

Although two RF conductors 48 are illustrated in FIGS. 3 and 4, it is contemplated that a single conductor 48 or a plurality of more than two conductors 48 may also be positioned about the exterior of the device 10.

As previously mentioned, the RF conductor or conductors 48 forms an electrical connection between the medical lead 42 and the circuitry of the device 10. However, multiple electrical connections may be established between the medical lead 42 and the circuitry of the device 10. One example is shown in FIG. 3, whereby both the RF conductor 48 and at least one intermediate conductor 44, make electrical connection between the medical lead 42 and the conductor connection 46 and the circuitry of the device 10.

In the case of the use of a plurality of RF conductors 48, each of the plurality of wires may be connected to a respective lead terminal 40. Alternatively, the RF conductor 48 may be selectively connected to a specific conductor lead 42. Furthermore, not all conductor leads 42 may be connected to an RF conductor 48. For example, a neurostimulator may comprise 24 electrode channels having 24 terminals within its header assembly 12. Therefore, there may be 24 separate RF conductors 48 that are electrically connected to each of the electrode channels. Furthermore, the header assembly 12 may be designed with fewer than 24 connections established between the electrodes and RF conductors 48.

In a preferred embodiment, each RF conductor 48 is made of a conductive material. More specifically, the RF conductor 48 may be made of titanium, MP35N, stainless steel, platinum, palladium, silver core MP35N, platinum core MP35N or another high purity biocompatible metal. Each RF conductor 48 may comprise the form of a single wire or filar strand as well as may be formed of a plurality of wires or filar strands in either a coiled, co-radial, coaxial, braided, twisted, cable, or combination thereof. Additionally, each RF conductor 48 may be fully or partially insulated to prevent shorting or coupling to any nearby conductive members or the medical device 10. It is further preferred that each wire or filar have a diameter that ranges from about 0.01 mm to about 0.5 mm. Furthermore, the RF conductor 48 may comprise a filled via or additionally a conductive trace, such as that of a line of a deposited conductive material.

Figure 8:
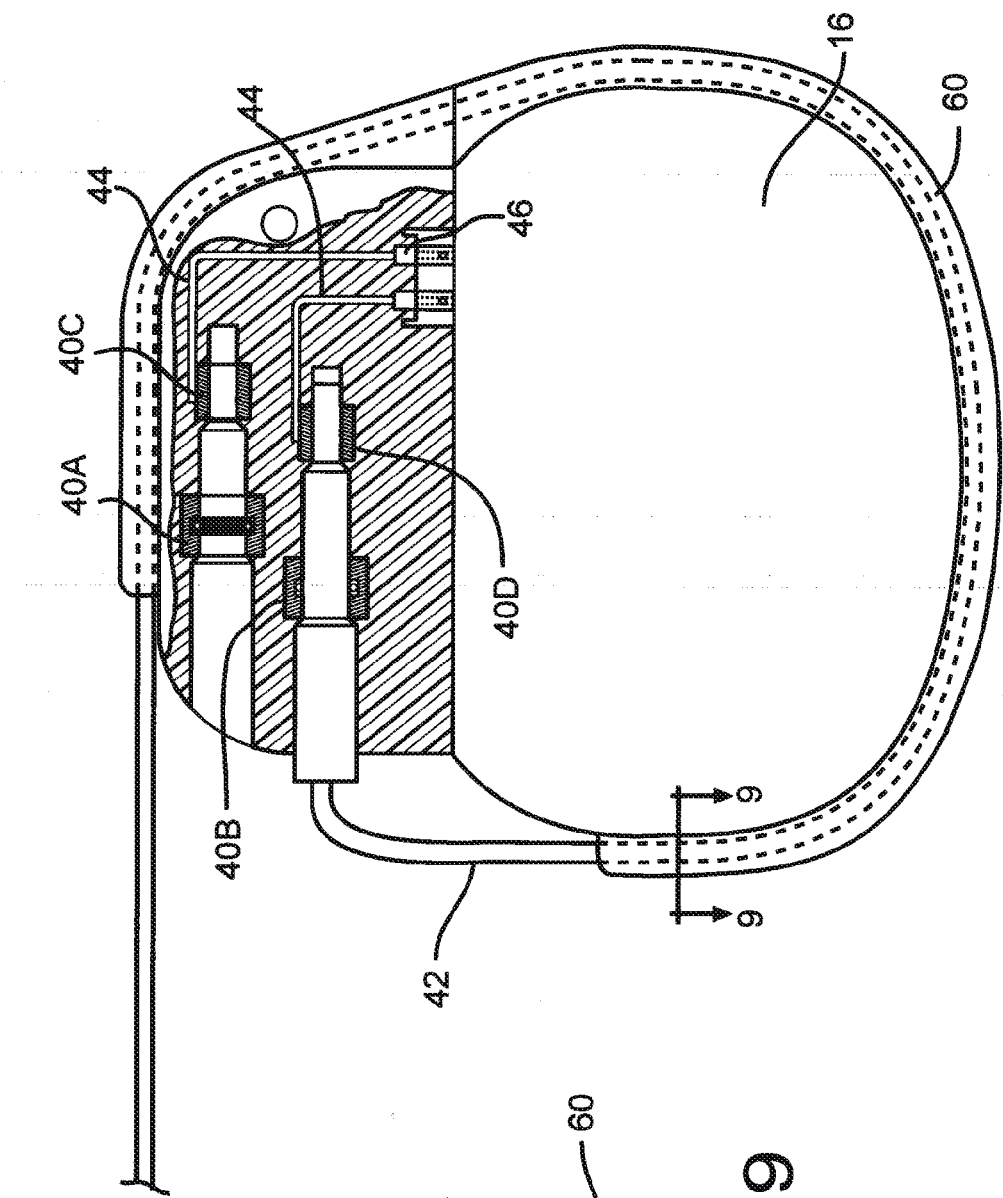
FIG. 8 shows a side view of an alternate embodiment of the present invention in which a medical lead is positioned about the perimeter of the device, the lead positioned within a covering.

FIGS. 5 through 9 illustrate an alternate embodiment of the present invention in which a conductor lead or medical lead 42 is positioned about the medical device 10. In a preferred embodiment, the medical lead 42 is positioned about the exterior of the housing 14 of the medical device 10 such that the lead 42 extends along the exterior surface of the sidewall in a controlled manner about the medical device 10. As shown in FIGS. 5 and 8, the lead 42 is positioned circumferentially around the device 10. More specifically, the medical lead 42 is positioned circumferentially along the exterior surface 24 of the left sidewall 52 of the housing 14, continuing along the exterior surface 25 of the bottom sidewall 56 and extending further along the exterior surface 26 of the right sidewall 50 of the housing 14 of the device 10.

Alternatively, the conductor lead 42 may be positioned such that it lies about perpendicular to imaginary plane 54 along the exterior of the housing 14. In other words, the conductor lead 42 may be positioned about parallel to imaginary longitudinal axis A-A such that it generally extends equatorially around the face walls 16, 18 of the device 10. Likewise, the medical lead 42 may be positioned about parallel to perpendicular axis B-B such that the lead extends from the bottom of the housing 14 to the top of the header assembly 12.

As shown, the proximal end 42A of the medical lead 42 is positioned within the insulative body 36 of the header assembly 12 of the medical device 10. Examples of possible header assembly configurations include, but are not limited to, IS-1, DF-1, IS-4 and DF-4 connectors. The design of the medical lead 42 is non-limiting and may include any of a variety of leads configured for use with a pacemaker, a defibrillator, a neurostimulator and the like. The present invention is non-limiting in that the incorporation of the conductor lead 42 may be utilized with any medical lead 42, regardless of its length or diameter. Furthermore, any medical lead regardless of its medical therapy, whether the lead is designed for cardiac pacing, cardiac defibrillation, neurostimulation or bone stimulation may be utilized with any of the embodiments of the present invention.

Examples of suitable medical leads include the Greatbatch Myopore™ sutureless unipolar and bipolar epicardial leads. Other examples may include the neurostimulator lead disclosed in U.S. Pat. No. 7,640,064 to Swoyer as well as leads disclosed in U.S. Pat. Nos. 5,143,090 and 5,255,693 to Dutcher et al. and U.S. Pat. No. 7,899,551 to Westlund et al. In addition, medical leads disclosed in U.S. Pat. No. 8,155,760 to Kondabatni et al. and U.S. Pat. No. 8,260,435 to Johnson et al. may also be used with the present invention. The present invention is further non-limiting in that medical leads incorporating MRI filtering technologies such as bandstop filters, component networks and the like therewithin may be utilized.

Figure 9:
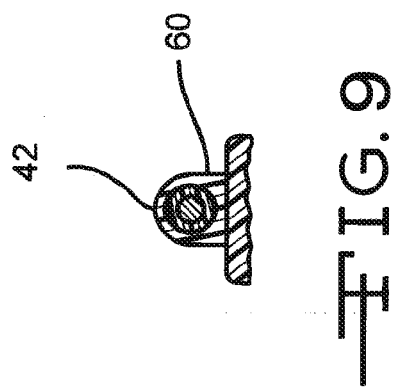
FIG. 9 illustrates a cross-sectional view taken along line 9-9 of FIG. 8.

As shown in FIGS. 5-7 and 10-11, a clip 58 may be used to hold the medical lead 42 in place against the external surface of the housing 14 of the device. In a preferred embodiment, as shown in FIGS. 5-7, a series of clips 58 are positioned around the exterior of the device 10 such that the lead 42 conforms to the contour of the exterior surface of the housing 14. Alternatively, as shown in FIGS. 8 and 9, the medical lead 42 may be positioned within a sleeve 60 that is attached to the housing 14 of the device 10. It is contemplated that these clip 58 and sleeve 60 features may also be used to hold the RF conductor or conductors 48 in place around the device 10. These sleeve and clip embodiments are designed to help keep the medical lead(s) 42 or RF conductor(s) 48 in position about the device 10 and to prevent the lead(s) 42 or RF conductor(s) 48 from becoming askew from its desired position.

Additionally, the sleeve 60 and clip 58 features prevent movement of the medical lead 42 due to what is commonly referred to as Twiddler's Syndrome. In Twiddler's Syndrome, a patient is prone to move the medical lead 42 and/or the medical device 10 to a different position from its original implanted position. A patient with Twiddler's Syndrome could, therefore, move the lead 42 or RF conductor 48 from its desired position with respect to imaginary plane 54 around the housing 14 of the device 10.

Furthermore, the clip 58 and/or the sleeve 60 features may be used to position an abandoned lead conductor or conductors about the exterior of the device 10. For example, the abandoned lead may be clipped by itself or alongside an active lead conductor 42 about the exterior of the device. Such a feature prevents the possibility of abandoned lead migration within the body as well as provides reduced RF induced current within the abandoned lead.

As illustrated in FIGS. 10 and 11, the medical lead 42 may be positioned along the exterior surface of either or both the major front or back device housing sidewalls 16, 18. In this configuration, the lead 42 is positioned such that it generally resides parallel to the plane of the major sidewalls 16, 18. The medical lead 42 is further positioned such that it generally outlines the perimeter of the housing 14 of the device 10. In a preferred embodiment, the medical lead 42 is positioned at about the outer edge of the housing 14 such that the medical lead 42 does not extend past the outer edge of the housing 14.

Similar to the previous embodiments, the lead 42 is positioned such that the outlined perimeter of the device 10 lies within the imaginary plane 54 and generally lies perpendicular to perpendicular axis A-A. Alternatively, the lead 42 may be positioned perpendicular to imaginary plane 54 such that the medical lead 42 extends equatorially around the device. A clip 58 or sleeve 60 may be positioned along the sidewall 16, 18 of the device to ensure the medical lead 42 is secure.

Figure 12:
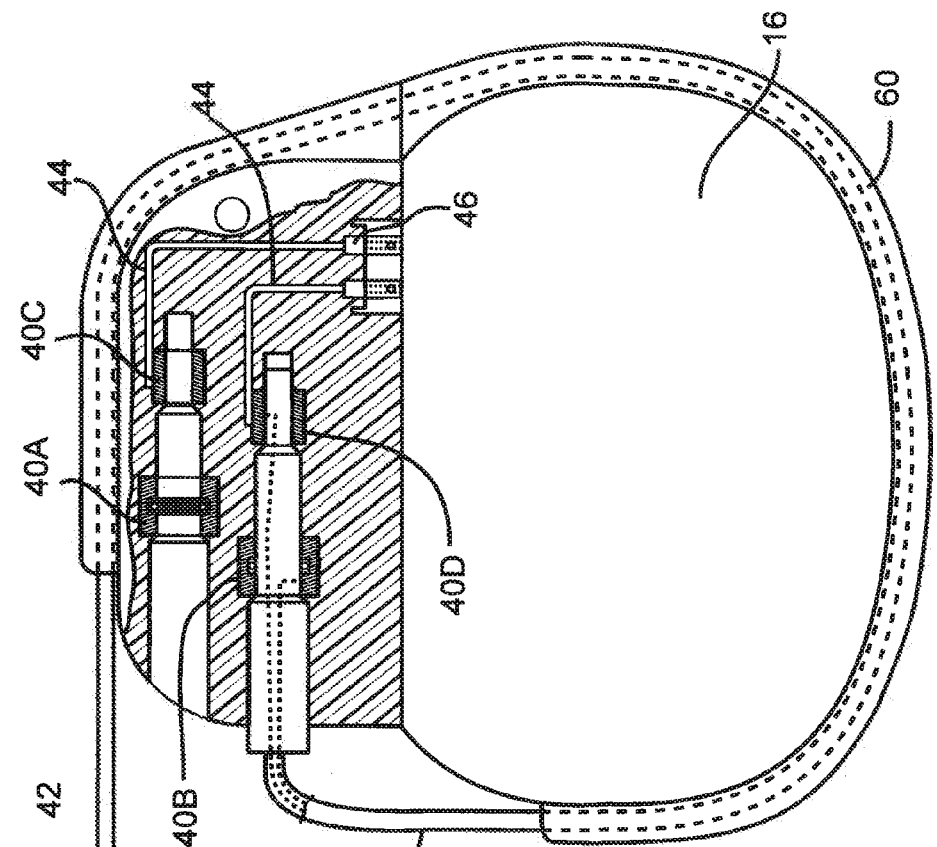
FIG. 12 illustrates a side view of an alternate embodiment of the present invention in which a lead extender 62 resides at the distal end of the conductor lead 42.
Figure 12A:
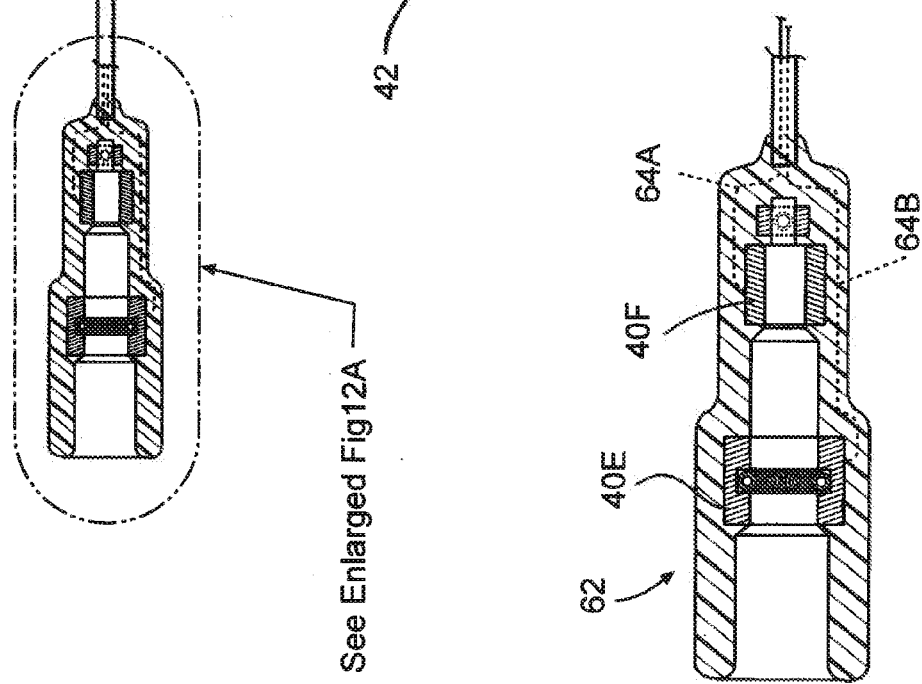
FIG. 12A shows a magnified view of the lead extender 62 shown in FIG. 12.

FIGS. 12 and 12A illustrate an alternate embodiment of the present invention. As illustrated, a lead extender 62 is shown. In this embodiment, an additional lead conductor 42 may be positioned therewithin. Specifically, the proximal end 42A of a second conductor lead 42 is placed within the opening of the extender 62. The proximal end 42A of the second lead conductor 42 establishes electrical contact with the terminal 40E, 40F. In a preferred embodiment, the extender may be designed similarly to that of an IS-1, DF-1, IS-4 or DF-4 lead connector. In a preferred embodiment, the lead extender 62 may be composed of an insulative material. Specifically, the extender 62 may be composed of a material similar to that of the insulative body 36 of the header assembly 12, such as silicone or TECOTHANE®.

When a second lead conductor 42 is placed within the extender 62, electrical connection is made between the proximal end 42A of the second conductor 42, within the extender 62 and the medical device. Specifically, extender conductors 64A, 64B establish electrical conduction between the existing lead and the second lead. Alternatively, the extender conductors 64A, 64B may make direct contact with the terminal residing within the insulative body 36 of the header assembly 12 of the medical device. The lead extender 62 enables the length of the lead to be extended such that an additional length of lead 42 may be positioned around the device.

Figure 13:
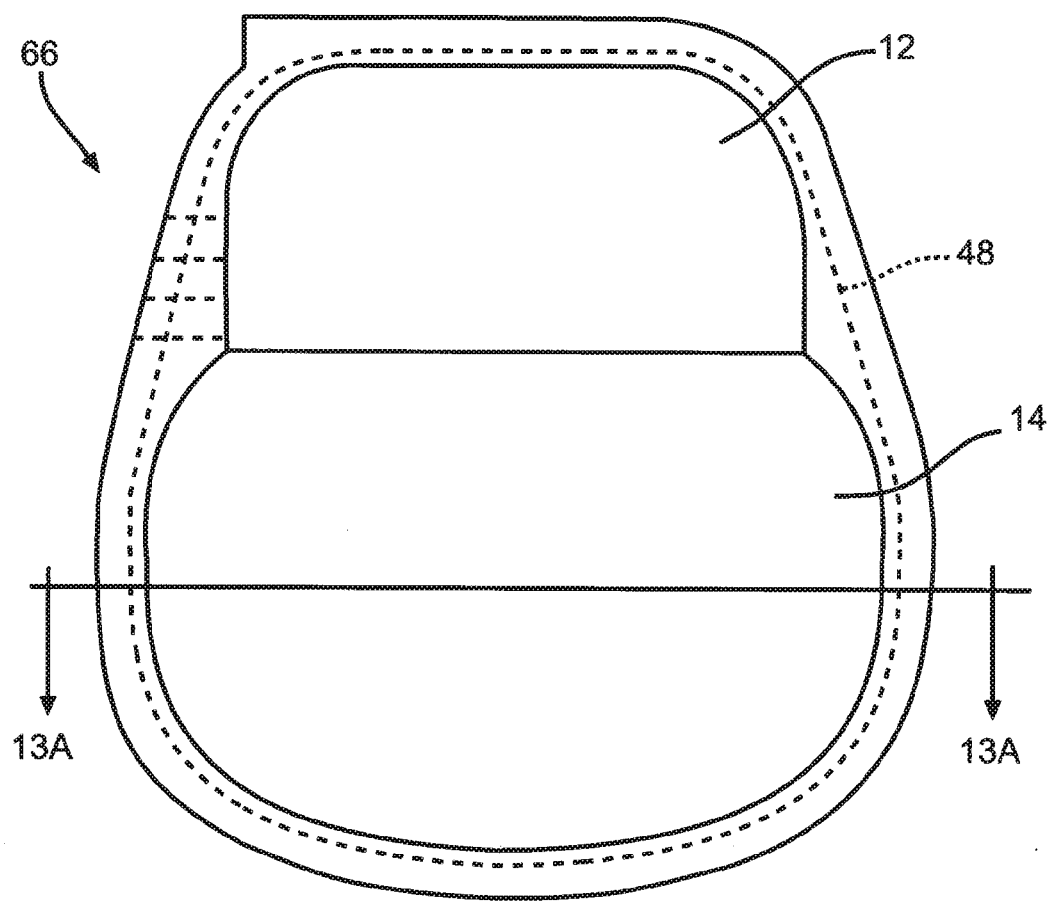
FIG. 13 shows a side view of an alternate embodiment in which an active implantable medical device resides within a device enclosure.
Figure 13A:
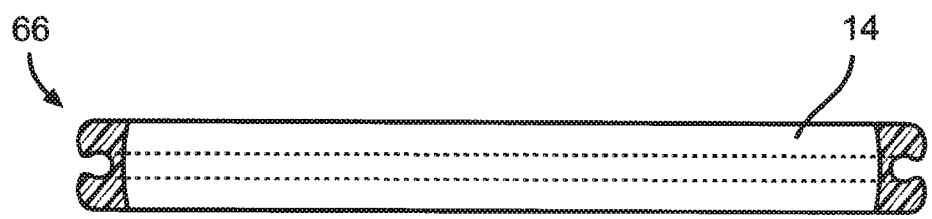
FIG. 13A illustrates a cross-sectional view taken along line 13A-13A.

FIGS. 13 and 13A illustrate an embodiment of a device enclosure 66. In a preferred embodiment, the medical device 10 is positioned within the enclosure 66 such that an RF conductor 48 may be positioned circumferentially around the device. As illustrated, the enclosure 66 is designed to conform to the exterior surface of the medical device 10. Specifically, the device enclosure 66 is designed to surround the device 10. An enclosure through-bore 65 provides a space through which the proximal end portion of the conductor lead 42A slides through to connect to the device 10. Alternatively, a conductor lead 42 may be positioned within the enclosure 66 such that the lead 42 is positioned circumferentially around the device 10.

As illustrated a single RF conductor 48 is positioned within the enclosure 66 and around the device. However, it is contemplated that multiple RF conductors 48 or leads 42 may be positioned within the thickness of the enclosure 66 and around the device 10. Furthermore, the RF or lead conductors may be positioned off axis or askew from the longitudinal or perpendicular axis of the device 10. It is further contemplated that conductors 42, 48 may be positioned anywhere within the wall thickness of the enclosure 66. In a preferred embodiment, the enclosure 66 may be made from an insulative material. Specifically, the enclosure may be composed of a silicone or TECOTHANE® material.

FIGS. 14 and 14A further illustrate an embodiment, in which a band 68 is positioned around the device. As illustrated, the band 68 is positioned around equatorially around the device 10. Within the band 68, preferably comprises a RF conductor 48 or conductor lead 42. More specifically, the RF conductor 48 or conductor lead 42 may reside within a thickness of the band 68. The band 68 enables the RF conductor 48 or lead conductor 42 to be positioned anywhere about the exterior surface of the body of the device. As shown in FIGS. 14 and 14A, the band 68 is positioned over the enclosure 66 as previously discussed. However, the band 68 may be positioned about the device 10 without the enclosure 66.

Similarly to the enclosure embodiment 66, previously discussed, the band 68 may be comprised of an insulative material. Specifically, the band 68 may comprise silicone, TECOTHANE® or other biocompatible material.

Accordingly, the invention is not limited, except by the appended claims.

What is claimed is:

1. An implantable medical device, comprising:
   a) a housing;
   b) a hermetic feedthrough terminal comprising a ferrule supporting an insulative material sealing between at least one conductive lead wire and an inner surface of the ferrule, wherein the ferrule is hermetically sealed in an opening in the housing, and wherein the conductive lead wire extends from a lead wire proximal portion electrically connected to electronic circuits disposed within the device housing remote from the ferrule to a lead wire distal end located outside the housing;

c) an intermediate conductor extending from an intermediate conductor proximal end to an intermediate conductor distal end, wherein the intermediate conductor proximal end is electrically connected to the lead wire distal end and wherein the intermediate conductor distal end is electrically connected to a terminal, the terminal being configured to detachably electrically connect to a lead;

d) an insulative header mounted on the device housing and encasing the intermediate conductor connecting from the lead wire distal end to the terminal;

e) a connector comprising a connector distal portion spaced from a connector proximal portion, the connector distal portion supported by the insulative body and electrically connected to the intermediate conductor second end, the connector proximal portion electrically connected to the at least one feedthrough conductor distal end extending external the housing; and f) an RF conductor comprising an RF conductor proximal end spaced from an RE conductor distal end, wherein the RE conductor proximal end is electrically connected to the connector with an RE conductor intermediate portion between the proximal and distal ends exiting the insulative header at an exit location and extending along an outer surface of the housing before entering the insulative header at an entry location spaced from the exit location and wherein the RE conductor distal end is electrically connected to the terminal.

2. The implantable medical device of claim 1 wherein the RF conductor is positioned longitudinally around the housing.

3. The implantable medical device of claim 1 wherein the RF conductor is positioned circumferentially around the housing.

4. The implantable medical device of claim 1 wherein the RF conductor is positioned equatorially around the housing.

5. The implantable medical device of claim 1 wherein the RF conductor extends less than one turn around the housing.

6. The implantable medical device of claim 1 wherein the RF conductor extends more than one turn around the housing.

7. The implantable medical device of claim 1 wherein the RF conductor comprises a metallic material.

8. The implantable medical device of claim 7 wherein the metallic material is selected from the group consisting of titanium, platinum, palladium, MP35N, stainless steel, and alloys thereof.

9. The implantable medical device of claim 1 wherein the RF conductor is at least partially insulated.

10. The implantable medical device of claim 1 wherein the RF conductor comprises a wire, a conductive trace, or a filar.

11. The implantable medical device of claim 1 wherein the RF conductor comprises a plurality of wires or filars.

12. The implantable medical device of claim 11 wherein the plurality of wires of filars are arranged in a form comprising a weave, a braid, a cable, a coil, a coaxial coil, a co-radial coil, a wound coil, or a twist.

13. The implantable medical device of claim 1 wherein the RF conductor is positioned within a series of clips that reside on an exterior surface of the housing for the implantable medical device.

14. The implantable medical device of claim 1 wherein the RF conductor is contacted to an exterior surface of the housing for the implantable medical device.

15. The implantable medical device of claim 1 wherein the housing is positioned within an enclosure having a wall thickness, and wherein the RF conductor is positioned within the enclosure wall thickness.

16. The implantable medical device of claim 1 wherein a band having a U-shaped recess is positioned around an exterior surface of the housing for the implantable medical device, and wherein the RF conductor resides within the recess of the band.

17. The implantable medical device of claim 1 wherein the implantable medical device is selected from the group consisting of a hearing assist device, a neurostimulator, a cardiac pacemaker, a drug pump, a cardiac defibrillator, a bone growth stimulator, and an obesity control device.

18. An implantable medical device system, comprising:

a) at least one implantable lead extending from a lead proximal end to a lead distal portion;

b) at least one electrode electrically connected to the lead distal portion, wherein the electrode is configured to be placed in contact with biological cells inside a body;

c) a housing;

d) a control circuitry connected to a power supply residing within the housing;

e) at least one feedthrough conductor having a feedthrough conductor proximal end spaced from a feedthrough conductor distal end, wherein the feedthrough conductor proximal end is positioned within the housing electrically connected to the control circuitry and the feedthrough conductor distal end extends external of the housing;

f) an electrically insulative body mountable on an exterior surface of the housing, wherein the insulative body has at least one inlet that extends within the body from an insulative body exterior surface;

g) a terminal block residing within and supported by the insulative body in open communication with the inlet, the terminal block having a throughbore extending therethrough configured to receive and electrically contact the lead proximal end inserted into the insulative body inlet;

h) an intermediate conductor comprising an intermediate conductor first end connected to the terminal block, and an intermediate conductor second end;

i) a connector comprising a connector distal portion spaced from a connector proximal portion, the connector distal portion supported by the insulative body and electrically connected to the intermediate conductor second end, the connector proximal portion electrically connected to the at least one feedthrough conductor distal end extending external the housing; and j) wherein with the lead proximal end inserted into the inlet and received in the terminal block throughbore, the lead has sufficient length to extend around at least a portion of an exterior circumference of the housing for the medical device such that RF current through the lead is modified from a first RF current had the lead not been positioned extending around the portion of the exterior circumference to a second RF current that is less than the first RF current.

19. The implantable medical device system of claim 18 wherein the lead is positioned longitudinally about the housing for the implantable medical device.

20. The implantable medical device system of claim 18 wherein the lead is positioned equatorially about the housing for the implantable medical device.

21. The implantable medical device system of claim 18 wherein the lead is positioned circumferentially around the housing for the implantable medical device.

22. The implantable medical device system of claim 18 wherein the lead is positioned such that it completes at least a full circumference of the housing for the implantable medical device.

23. The implantable medical device system of claim 18 wherein the lead completes less than a full circumference about the housing for the implantable medical device.

24. The implantable medical device system of claim 18 wherein the lead is positioned within a series of clips that extend from an exterior surface of the housing.

25. The implantable medical device system of claim 18 wherein the lead is positioned within a sleeve that is supported on an exterior surface of the housing for the implantable medical device.

26. The implantable medical device system of claim 18 wherein the housing is positioned within an enclosure having a wall thickness, and wherein the lead is positioned within the enclosure wall thickness.

27. The implantable medical device system of claim 18 wherein a band having a U-shaped recess is positioned around an exterior surface of the housing, and wherein the lead resides within the recess of the the band.

28. The implantable medical device system of claim 18 wherein the device is selected from the group consisting of a hearing assist device, a neurostimulator, a cardiac pacemaker, a drug pump, a cardiac defibrillator, a bone growth stimulator and an obesity control device.

29. The implantable medical device system of claim 18 wherein the lead is comprised of a plurality of electrically conductive wires or filars.

30. The implantable medical device system of claim 18 wherein the plurality of wires or filars are arranged in a form comprising a cable, a braided, a co-radial, or combination thereof.

31. The implantable medical device system of claim 18 wherein a lead extender connects a distal end of the lead distal portion to a proximal end of a second conductor lead to thereby provide a third lead system having a longer total length than either of the first and second leads.

32. An implantable medical device, comprising:
a) a housing;
b) a control circuitry electrically connected to at least one electrical energy storage device positioned within the housing;
c) an electrically insulative body mounted on an exterior surface of the housing, wherein the electrically insulative body has at least one inlet that extends within the body from an insulative body exterior surface, the insulative body inlet adapted to receive an end of a lead configured to provide therapeutic electrical stimulation to tissue;
d) at least one terminal block that resides within and is supported by the insulative body, wherein the at least one terminal block has a throughbore extending therethrough configured to receive and electrically connect to the lead;
e) at least one feedthrough conductor having a feedthrough conductor distal end spaced from a feedthrough conductor proximal end, the feedthrough conductor proximal end positioned within the housing and electrically connected to the control circuitry that resides within the housing, wherein the feedthrough conductor distal end resides external of the housing;
f) an RF conductor having an RF conductor first end spaced from an RF conductor second end, wherein the RE' conductor first end is electrically connected to the at least one terminal block positioned within the insulative body and the RF conductor second end is electrically connected to the at least one feedthrough conductor distal end;
wherein when the lead is electrically connected to the terminal block, an RF current within the lead is modified from a first RF current to a second RF current that is less than the first RF current.

\* \* \* \* \*

UNITED STATES PATENT AND TRADEMARK OFFICE
CERTIFICATE OF CORRECTION

PATENT NO. : 9,061,132 B1
APPLICATION NO. : 13/400701
DATED : June 23, 2015
INVENTOR(S) : Jeffrey Zweber and Robert Shawn Johnson It is certified that error appears in the above-identified patent and that said Letters Patent is hereby corrected as shown below:

Claims

Column 13, line 22 (Claim 1, line 30) delete "RE" and insert --RF--

Column 13, line 23 (Claim 1, line 31) delete "RE" and insert --RF--

Column 13, line 24 (Claim 1, line 32) delete "RE" and insert --RF--

Column 13, line 29 (Claim 1, line 37) delete "RE" and insert --RF--

Column 16, line 1 (Claim 31, line 3) after the word "second" delete the word "conductor"

Column 16, line 29 (Claim 32, line 26) delete "RE'" and insert --RF--

Signed and Sealed this
First Day of March, 2016

Michelle K. Lee
*Director of the United States Patent and Trademark Office*